United States Patent [19]

Naujokas

[11] Patent Number: 5,672,729

[45] Date of Patent: Sep. 30, 1997

[54] RECOVERY OF TEREPHTHALATE DIESTERS FROM GLYCOL RESIDUES

[75] Inventor: Andrius Algimantas Naujokas, Webster, N.Y.

[73] Assignee: Eastman Kodak Company, Rochester, N.Y.

[21] Appl. No.: 696,556

[22] Filed: Aug. 14, 1996

Related U.S. Application Data

[60] Provisional application No. 60/002,072, Jul. 28, 1995 and Provisional Application No. 60/002,179, Aug. 11, 1995.

[51] Int. Cl.$^6$ .................................................. C07C 67/62
[52] U.S. Cl. ........................................................ 560/78
[58] Field of Search ........................................... 560/78

[56] References Cited

U.S. PATENT DOCUMENTS

| | | | |
|---|---|---|---|
| 3,949,007 | 4/1976 | Grolig et al. | 260/635 |
| 4,163,860 | 8/1979 | Delattre et al. | 560/96 |
| 5,051,528 | 9/1991 | Naujokas et al. | 560/78 |
| 5,298,530 | 3/1994 | Gamble et al. | 521/48.5 |
| 5,393,916 | 2/1995 | Gamble et al. | 560/78 |
| 5,414,022 | 5/1995 | Toot, Jr. et al. | 521/48 |
| 5,432,203 | 7/1995 | DeBruin et al. | 521/48.5 |
| 5,578,173 | 11/1996 | Toot, Jr. et al. | 203/6 |

FOREIGN PATENT DOCUMENTS 1081681  12/1954  France .

*Primary Examiner*—Samuel Barts
*Attorney, Agent, or Firm*—Joshua G. Levitt

[57] ABSTRACT

There is described a process for improving the yield of difunctional ester in a process of recovering monomer components from condensation-type polyester resins such as polyethylene terephthalate by converting terephthalyl monomers and oligomers present in ethylene glycol still bottoms to terephthalate diester, such as dimethyl terephthalate. This is accomplished by treating the terephthalyl monomers and oligomers with a mixture of an alcohol and an alkali metal hydroxide at a temperature up to the boiling point of the alcohol.

7 Claims, 2 Drawing Sheets

RECOVERY OF TEREPHTHALATE DIESTERS FROM GLYCOL RESIDUES

CROSS REFERENCE TO RELATED APPLICATIONS

U.S. Provisional patent application Ser. No. 60/002,072 filed Jul. 28, 1995, (now U.S. patent application Ser. No. 08/678,006, filed Jul. 10, 1996) of Andrius A. Naujokas, for Recovery of Ester Monomers from Polyester Resins, relates to a process for the conversion of a mixture of dimethyl terephthalate and methylhydroxyethyl terephthalate to predominantly dimethyl terephthalate by treating that mixture with an alcohol and an alkali metal hydroxide.

U.S. Provisional patent application Ser. No. 60/002,179 filed Aug. 11, 1995, (now U.S. patent application Ser. No. 08/687,822, filed Jul. 26, 1996 of William J. Gamble and Andrius A. Naujokas, for Purification of Ethylene Glycol Recovered from Polyester Resins, relates to a process for removing dimethyl terephthalate contaminants from ethylene glycol by use of an ester exchange catalyst.

FIELD OF INVENTION

This invention relates to a process for improving the yield of difunctional ester in a process of recovering monomer components from condensation-type polyester resins such as polyethylene terephthalate. In particular it relates to a process for converting terephthalyl monomers and oligomers present in ethylene glycol still bottoms to terephthalate diester, such as dimethyl terephthalate, for recovery of the latter.

BACKGROUND OF THE INVENTION

Polyester resins have found widespread use in varied applications. Polyester resins, such as polyethylene terephthalate, are used in films, including photographic film, in fibers, and in food and beverage containers. Various methods have been disclosed for the depolymerization of such resins into their component monomers, such as ethylene glycol and terephthalic acid, or derivatives thereof, so that they could be reused.

Some of these methods are described in such patents as U.S. Pat. Nos. 3,037,050, 3,321,510, 3,884,850, 3,907,868, 4,163,860, 4,578,502, 4,620,032, 4,876,378 and 5,095,145, and in European Published Patent Application 0 484 963 published May 13, 1992.

A particularly useful technique for recovering monomer components from scrap polyester is low pressure methanolysis, which is described in a series of patents that begins with Naujokas et al. U.S. Pat. No. 5,051,528. This patent describes a process of recovering ethylene glycol and dimethyl terephthalate from polyethylene terephthalate scrap resins by dissolving the polyester resin in oligomers of the same monomers as present in the polyester, passing superheated methanol through the solution and recovering ethylene glycol and dimethyl terephthalate.

Gamble et al. U.S. Pat. No. 5,298,530, issued Mar. 29, 1994 describes improvements in this process. In the improved process scrap resin is combined in a dissolver with melt from the reactor to form a dissolver melt, and the dissolver melt is transferred to the reactor for contact with super-heated methanol. In the reactor, polymers and oligomers are further depolymerized into component glycol and ester monomers, which are then recovered.

Further improvements and variations of this process are described in Gamble et al. U.S. Pat. No. 5,393,916 issued Feb. 28, 1995 and in Toot et al. U.S. Pat. No. 5,414,022 issued May 9, 1995.

The processes described in these patents reverse the polymerization reaction by which the polyethylene terephthalate is formed by depolymerizing polyethylene terephthalate (PET) to dimethyl terephthalate (DMT) and ethylene glycol (EG). DMT and EG are recovered and reused.

A typical process for the separation and recovery of dimethyl terephthalate and ethylene glycol is to, in the following order, remove excess methanol, crystallize dimethyl terephthalate, distill methanol and distill ethylene glycol. Although this recovery process is designed so that dimethyl terephthalate is removed first, since dimethyl terephthalate is soluble to a limited extent in the other components, some dimethyl terephthalate remains with the ethylene glycol that goes to the ethylene glycol distillation column. By the time the ethylene glycol is recovered, the dimethyl terephthalate has been converted to a mixture of terephthalyl monomers composed predominately of bishydroxyethyl terephthalate, but also comprising dimethyl terephthalate, methylhydroxyethyl terephthalate, and terephthalyl oligomers. This mixture is present in the still bottoms exiting the distillation column in which ethylene glycol is recovered. These ethylene glycol still bottoms also contain higher molecular weight glycols, such as diethylene glycol, triethylene glycol, etc., which are desirably recovered. The presence of the terephthalyl monomers and oligomers increases the viscosity of the still bottoms and complicates the recovery of the higher molecular weight glycols. Furthermore, since one of the principal purposes of the overall process is to obtain dimethyl terephthalate, the terephthalyl monomers present represent an additional source of that product.

Thus, it would be desirable to have a process for recovering terephthalate diesters, in particular dimethyl terephthalate, from the ethylene glycol still bottoms, so as to increase the yield of terephthalate diester and to facilitate the recovery of the higher molecular weight glycols present in the still bottoms.

SUMMARY OF THE INVENTION

I have found that a mixture of an alcohol and an alkali metal hydroxide acts as a catalyst for the conversion of terephthalyl monomers and oligomers present in the ethylene glycol still bottoms to dimethyl terephthalate, thus causing it to precipitate and be separable from the glycols and other components present in the liquid phase.

Thus, the present invention provides a process for converting a first mixture of terephthalyl monomers and oligomers to terephthalate diester by:

a) contacting the first mixture with a second mixture comprising an alcohol and an alkali metal hydroxide at a temperature in the range of from 0° C. to the boiling point of the alcohol and a pressure in the range of 0 psig to 100 psig, b) allowing the mixture formed in step a) to react for a period of from 0.5 to 30 minutes, and c) separating the terephalate diester formed in step b) from the liquid glycol residue.

Metal alkoxides are described in Grolig et al. U.S. Pat. No. 3,949,007 issued Apr. 6, 1976, Delattre e.t al U.S. Pat. No. 4,163,860 issued Aug. 7, 1979, and French Patent 1,081,681, published Dec. 22, 1954 (which is summarized in U.S. Pat. No. 4,163,860) for use as depolymerization or transesterification catalysts. However, the processes described in these patents are different from the present process and use the alkoxide at a different point for a different purpose.

The process of the present invention provides a simple, convenient way of increasing the yield of the diester obtained by the depolymerization of polyester resins.

DETAILED DESCRIPTION OF THE INVENTION

The present invention can be carried out as a batch process or a continuous process and can be applied to ethylene glycol still bottoms containing terephthalyl monomers from whatever source obtained.

The ethylene glycol still bottoms are contacted with a mixture of an alkali metal hydroxide in an alcohol. Preferred alkali metal hydroxides are sodium hydroxide and potassium hydroxide, although others can be used. If the ester desired is dimethyl terephthalate, the alcohol used is methanol. If a different ester is desired, the corresponding alcohol is used, for example ethanol, propanol, butanol, hexanol, etc. Thus, the alcohol can be an alkanol of 1 to 6 carbon atoms and the corresponding alkyl diester will be recovered. For ease of discussion, this application discusses recovery in the context of dimethyl terephthalate, but it will be appreciated that other terephthalate diesters could be obtained by the substitution of the appropriate alcohol.

The proportions of alkali metal hydroxide to alcohol are not critical. There should be at least sufficient alcohol to react with the terephthalyl components (TM&O) to convert them to dimethyl terephthalate (DMT). Typically, the mixture can comprise about 1 to 10 parts alkali metal hydroxide per 100 parts alcohol (by weight). The mixture of alkali metal hydroxide in alcohol is contacted with the TM&O to convert it to DMT. This can be accomplished at a temperature from about 0° C. to the boiling point of the alcohol used (64° C. for methanol at atmospheric pressure) and at a pressure from atmospheric pressure to elevated pressure. Preferably the reaction is carried out at temperatures from about 15° C. to about 30° C. and a pressure of 0 to 30 psig.

The amount of the mixture of alkali metal hydroxide in alcohol contacted with the TM&O can vary over a wide range. Typically, from about 0.5 to 2.0 part by weight of the mixture of alkali metal hydroxide in alcohol is used per part by weight of the TM&O mixture. The time of contact will vary depending upon the particular composition of the TM&O. Contact times of from several seconds to several minutes provide useful results.

The process of this invention can be performed as a batch process using TM&O from whatever source derived. In a preferred embodiment, the present invention is applied to mixtures of DMT and MHET obtained from low pressure methanolysis apparatus as described in U.S. Pat. No. 5,051,528.

In one embodiment, the alcohol/alkali metal hydroxide mixture can be introduced into a holding tank with the ethylene Glycol still bottoms where they are allowed to react and then sent to a filtration device where the dimethyl terephthalate is removed. In yet another embodiment, the alcohol/alkali metal hydroxide mixture can be added to the ethylene Glycol still bottoms as they are being transported from the ethylene Glycol distillation column to the filtration device.

Figure 1:
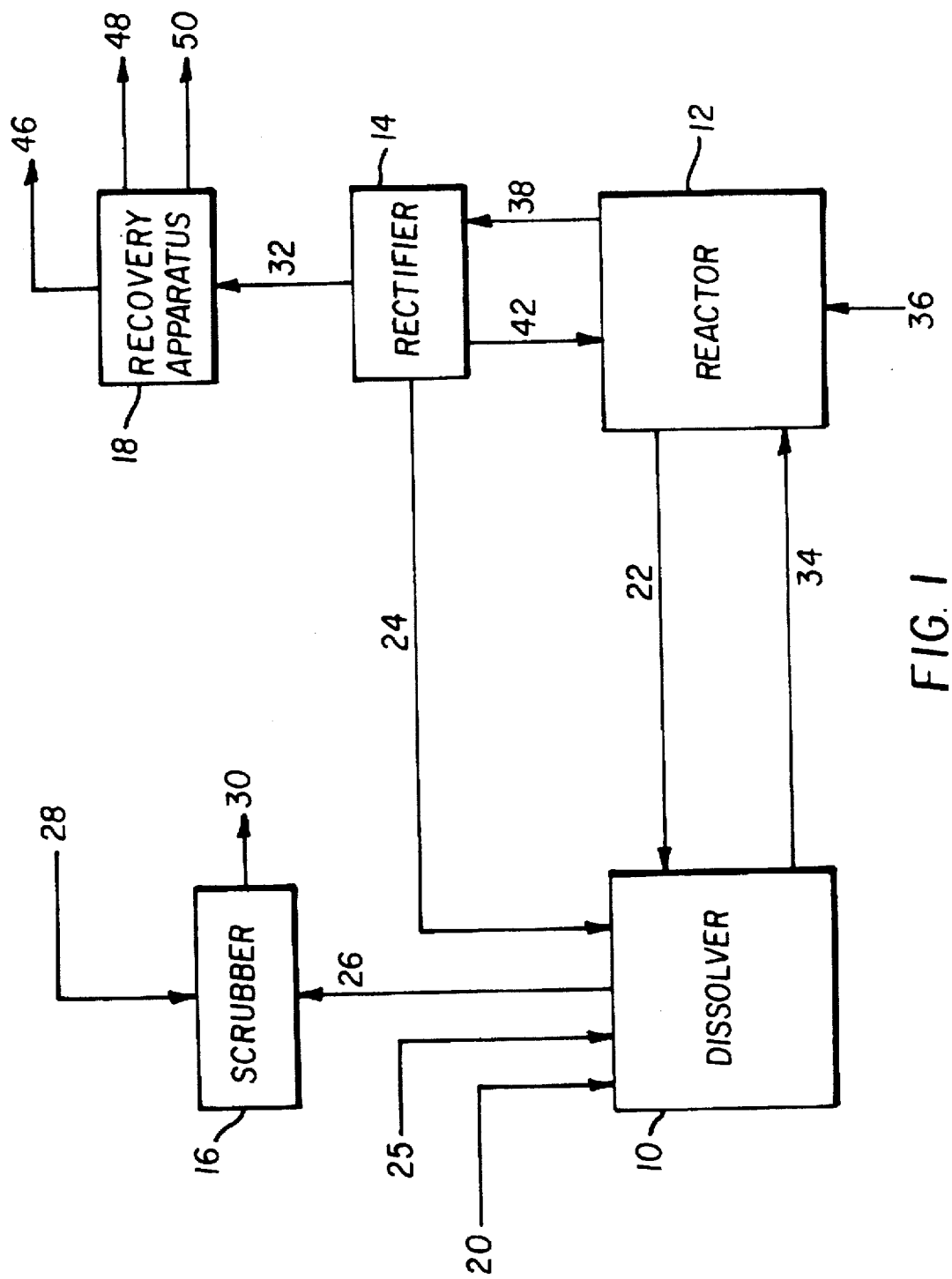
FIG. 1 is a schematic flow diagram illustrating preferred apparatus for low pressure methanolysis of polyester resins.

The present invention preferably is applied to ethylene Glycol obtained from the apparatus and process depicted in FIG. 1. It can utilize apparatus shown in FIG. 2, which is an elaboration of the recovery apparatus (18) shown in FIG. 1.

The apparatus of FIG. 1. comprises:
 a dissolver for receiving polyester,
 a reactor for depolymerizing polyester into monomer components, and
 recovery apparatus for separating reaction products.

This apparatus is used in a process which comprises the steps of:
 i) adding polyester to the dissolver and combining it with melt from the reactor to reduce the chain length of the polyester,
 ii) transferring reduced chain length polyester from the dissolver to the reactor,
 iii) passing super-heated methanol through the reactor to depolymerize polyester,
 iv) recovering monomer components from the output of the reactor to leave a residue comprising terephthalyl monomers, terephthalyl oligomers and ethylene glycol oligomers, and;
 b) applying the above described process to the residue obtained in a)iv).

The process and apparatus of FIG. 1 are described in detail in the Naujokas et al, Gamble et al. and Toot et al. patents referred to above, and the disclosures of those patents are incorporated herein by reference. In the apparatus of FIG. 1 a dissolver (10), a reactor (12), and a rectifier (14), are connected by the pipes, pumps and valves needed to transfer the reactants from one location to another in accordance with the reaction. Optionally included in this apparatus is a scrubber (16), for recovering gases from the dissolver.

In practice, polyethylene terephthalate (20) in a suitable form and size is introduced into the dissolver by any suitable means where it is liquefied and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

One or both of the reactor melt (22) and the rectifier liquid (24) can be introduced into the dissolver via suitable piping. Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst (25), such as zinc acetate. Such catalysts are known in the art to facilitate the depolymerization process.

The reactor melt and dissolver melt comprise methanol, low molecular weight polyesters, monomers, monohydric alcohol-ended oligomers, glycols, dimethyl terephthalate and methylhydroxyethyl terephthalate. The major difference between these two melts is the average chain length of the polyester. The rectifier liquid contains the same components except for polyesters.

The viscosity of the dissolver melt preferably is maintained in the range of 0.002 to 0.1 Pa. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) is then passed to the recovery apparatus (18) where it is combined with the vapor stream (32) exiting the rectifier for recovery.

Melt (34) from the dissolver is transferred to the reactor by suitable piping and pumps. Super-heated methanol vapor (36) is provided to the reactor by conventional means. The methanol introduced into the reactor heats the reactor contents and acts as a depolymerization agent. The effectiveness of the super-heated methanol for heating the reactor contents and for stripping reaction product depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, dimethyl terephthalate, glycols including ethylene glycol, diethylene glycol, and triethylene glycol, dimethyl isophthalate, cyclohexanedimethanol, and methylhydroxyethyl terephthalate. The rectifier separates the higher boiling components, such as methylhydroxyethyl terephthalate and esterification catalyst from the vapor stream exiting the reactor. They can be routed to the dissolver in the form of a liquid (24) together with dimethyl terephthalate, glycols and methanol or all or portion can be returned to the reactor as a liquid (42).

The remainder of the vapor stream (32) is transferred from the rectifier to recovery apparatus (18), where methanol (46) is recovered for further use, and the glycol components (48) separated from the terephthalate components (50). This is illustrated in more detail in FIG. 2.

Figure 2:
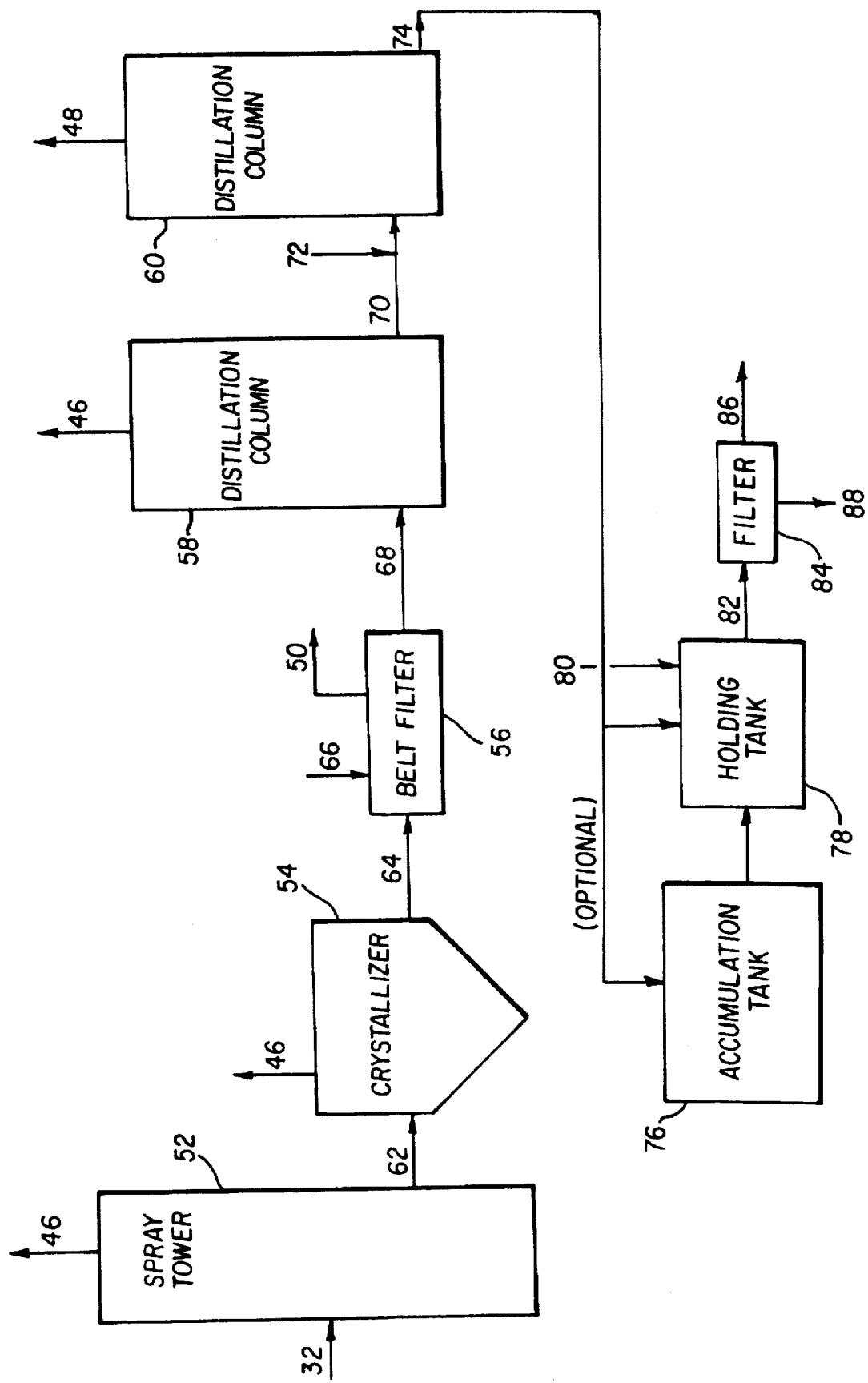
FIG. 2 is a schematic flow diagram illustrating preferred apparatus for the separation of the components recovered in accordance with FIG. 1 and for the recovery of terephthalate diester from the ethylene glycol still bottoms.

As shown in FIG. 2, the output of the rectifier, which principally comprises methanol, dimethyl terephthalate and ethlyene Glycol is sent to a spray tower (52), where the bulk of the methanol is removed. The spray tower is essentially a distillation column operated at a temperature in the range of 65° to 100° C. to condense the vapor stream exiting the rectifier. Methanol vapor is partially removed at the top of the column and the conditions of concentration and pressure are adjusted to maintained dimethyl terephthalate in solution. The solution (62) can be recirculated from the bottom of the tower to a higher level and sprayed on incoming vapor to facilitate cooling.

The solution (62), which comprises Glycol and terephthalate components in residual methanol, is transferred to a crystallizer (54) and then to a belt filter to recover dimethyl terephthalate (50). In the crystallizer the dimethyl terephthalate is concentrated, additional methanol is recovered and the dimethyl terephthalate is precipitated. The crystallizer is operated at a temperature in the range of 25° to 65° C. and at atmospheric pressure. In the belt filter the dimethyl terephthalate crystals are purified by washing with liquid methanol (66) at a temperature in the range of 20° to 40° C. The dimethyl terephthalate product (50) can then be sent to further recovery operations consistent with the use to which it will be put.

The effluent (68) of the belt filter contains methanol, ethylene Glycol and residual dimethyl terephthalate, and commonly will contain higher glycols, other terephthalates and oligomers. Methanol is separated from the other components in a first distillation operation. This can be accomplished in a distillation column (58) operated at the temperature of the boiling point of methanol 65° C. at atmospheric pressure.)

While the preceding procedure represents a preferred way of recovering ethylene Glycol, it will be appreciated that there are other ways of obtaining ethylene glycol which contains residual dimethyl terephthalate. The remainder of the discussion is applicable to ethylene glycol obtained by the procedure just described, or by other procedures.

The higher boiling components (70) exiting the first distillation column are transferred to a second distillation column (60) operated at a temperature in the range of 100° to 230° C. and a pressure in the range of 3 to 30 psia. Because dimethyl terephthalate has a relatively high melting point (140° C.) and a narrow liquid phase range, it has a propensity to sublime and form a solid deposit. Also, dimethyl terephthalate and ethylene glycol form an azeotrope which prevents their complete separation from one another. Thus, unless it is converted to a compound with different characteristics, it will foul the distillation column (60) and require more frequent shut down for cleaning than otherwise would be necessary. The addition of an ester exchange catalyst (72), such as zinc acetate, facilitates reaction between dimethyl terephthalate and ethylene glycol to form methylhydroxyethyl terephthalate, which has a higher boiling point and, hence, less of a propensity to foul the distillation column. The catalyst can be introduced anywhere in the ethylene glycol mixture downstream of the rectifier. A convenient location is to introduce the catalyst (72) into the stream (70) going from the first distillation column to the second distillation column, or into the second distillation column.

The output of the second distillation column (60) is ethylene glycol (48) and ethylene glycol still bottoms (74) which can be accumulated in an accumulation tank (76) and then recovered in accordance with this invention by sending them to a holding tank (78) where they are contacted with a mixture of an alcohol and an alkali metal hydroxide (80) and allowed to react. Alternatively, the accumulation tank can be bypassed and the still bottoms sent directly to the holding tank. The reaction mixture (82) is then sent to a filter (84), which can be similar to belt filter (56), where dimethyl terephthalate (86) is separated from the higher glycols (88).

The following examples illustrate the invention. Unless otherwise indicated, all percentages and parts are by weight.

EXAMPLE 1

The apparatus employed comprised a one liter three neck reaction flask equipped with a condenser, a heated dropping funnel and an electrically driven agitator. Caustic methanol was prepared by introducing 200 g methanol into the reaction flask and then adding 2.5 g sodium hydroxide pellets. The mixture was stirred until the solids dissolved. The temperature of the caustic methanol was about 26° C. Glycol still bottoms, which are solid at room temperature, were heated to 200° C. to obtain a liquid of suitable viscosity. 250 g of the molten still bottoms were then introduced into the dropping funnel attached to the reactor. With agitation, the molten still bottoms were then transferred within about 1 min. elapsed time from the dropping funnel to the reactor where they mixed with the caustic methanol. Within abut 30 sec. of the start of the addition, crystalline solids appeared in the reactor. The reaction was allowed to proceed to completion in 30 min and the mixture cooled to obtain a crop of crystals. Then the solids were separated from the slurry by filtration, were washed with fresh methanol and dried. Analysis of the DMT recovered, the slurry liquor remaining in the reactor and the methanol used to wash the DMT recovered showed the following:

| DMT | |
|---|---|
| Washed DMT: | 126.6 g |
| DMT Purity: | 90% |
| Slurry Liquor: | 1.6 g |
| Wash Methanol: | 2.6 g |
| Glycols (based on total glycols) | |
| Slurry Liquor: | 62% EG |
| | 32% DEG |
| | 6% TEG |
| Wash Methanol | 36% EG |
| | 53% DEG |
| | 11% TEG |

These results show that most of the terephthalyl group containing compounds in the slurry were converted to DMT, while the glycols remained in the slurry liquor.

EXAMPLE 2

Using the same apparatus as in Example 1, caustic methanol was prepared by adding 1% by weight of sodium hydroxide to methanol and dissolving the solids with agitation. 200 g. of diced solid Glycol still residue was added to 350 g. of the caustic methanol at room temperature. The mixture was allowed to react, with agitation, for about 2 hours until a uniform slurry was obtained. The slurry was filtered and then washed with fresh methanol. Analysis of the DMT recovered showed the following results:

| DMT | |
|---|---|
| Washed DMT: | 342 g |
| DMT Purity: | 65% |

These results show that the reaction can be carried out at room temperature using the solid still residue, although longer reaction times are required.

The invention has been described by reference to preferred embodiments, but it will be understood changes can be made to the apparatus and process steps specifically described herein within the spirit and scope of the invention.

What is claimed is:

1. A process for recovering terephthalate diester from a first mixture comprising terephthalyl monomers, terephthalyl oligomers and ethylene glycol oligomers comprising the steps of:

a) contacting the first mixture with a second mixture comprising an alcohol and an alkali metal hydroxide at a temperature in the range of from 0° C. to the boiling point of the alcohol and a pressure in the range of 0 psig to 100 psig, b) allowing the mixture formed in step a) to react for a period of from 0.5 to 30 minutes, and c) separating the terephalate diester formed in step b) from the liquid glycol residue.

2. A process of claim 1, wherein from 0.5 to 2 part by weight of the second mixture are contacted with 1 part of the first mixture.

3. A process of claim 1, wherein the second mixture comprises from 1 to 10 parts by weight alkali metal hydroxide per 100 parts alcohol.

4. A process of claim 1, wherein the alcohol is methanol and the terephalate diester recovered is dimethyl terephthalate.

5. A process of claim 1, wherein the alkali metal hydroxide is sodium hydroxide.

6. A process of claim 1, wherein the first mixture is formed by low pressure methanolysis.

7. A process for recovering dimethyl terephthalate from a first mixture comprising terephthalyl monomers, terephthalyl oligomers and ethylene glycol oligomers, the process comprising the steps of:

a) obtaining a mixture comprising terephthalyl monomers, terephthalyl oligomers and ethylene glycol oligomers using apparatus that comprises:

a dissolver for receiving polyester, a reactor for depolymerizing polyester into monomer components, and recovery apparatus for separating reaction products by i) adding polyester to the dissolver and combining it with melt from the reactor to reduce the chain length of the polyester, ii) transferring reduced chain length polyester from the dissolver to the reactor, iii) passing super-heated methanol through the reactor to depolymerize polyester, iv) recovering monomer components from the output of the reactor to leave a residue comprising terephthalyl monomers, terephthalyl oligomers and ethylene glycol oligomers, and;

b) applying the process of claim 4 to the residue obtained in a)iv).

* * * * *

IN THE UNITED STATES PATENT AND TRADEMARK OFFICE
CERTIFICATE OF CORRECTION

PATENT NO.: 5,672,729
DATED: September 30, 1997
INVENTOR(S): Andrius A. Naujokas It is certified that an error appears in the above-identified patent and that said Letters Patent is hereby corrected as shown below:

Cover page of Patent     Delete     "Related U.S. Application Data

[60] Provisional application No. 60/002,072, Jul. 28, 1995 and Provisional Application No. 60/002,179, Aug. 11, 1995."

Signed and Sealed this

Seventeenth Day of February, 1998

*Attest:*

BRUCE LEHMAN

*Attesting Officer*            *Commissioner of Patents and Trademarks*